(12) United States Patent
Frederick et al.

(10) Patent No.: US 7,901,411 B2
(45) Date of Patent: Mar. 8, 2011

(54) HIP REPLACEMENT INCISION LOCATOR

(75) Inventors: Phillip Frederick, Memphis, TN (US);
Russell Walter, Memphis, TN (US);
David Harwood, New Brunswick, NJ
(US); Robert Kepley, Akron, OH (US)

(73) Assignee: Smith & Nephew, Inc., Memphis, TN (US)

( * ) Notice: Subject to any disclaimer, the term of this patent is extended or adjusted under 35 U.S.C. 154(b) by 1117 days.

(21) Appl. No.: 11/036,469

(22) Filed: Jan. 14, 2005

(65) Prior Publication Data

US 2005/0277943 A1 Dec. 15, 2005

Related U.S. Application Data

(63) Continuation of application No. 10/775,561, filed on Feb. 10, 2004, now Pat. No. 7,160,307.

(51) Int. Cl.
*A61B 17/58* (2006.01)
*A61B 17/60* (2006.01)
*A61B 17/3209* (2006.01)
*A61F 2/46* (2006.01)

(52) U.S. Cl. .......... 606/102; 606/86 R; 606/87; 606/88; 606/89

(58) Field of Classification Search ............ 623/22.4, 623/23.11; 606/79, 82, 84, 86 R–89, 99, 606/102

See application file for complete search history.

(56) References Cited

U.S. PATENT DOCUMENTS

| 4,760,844 | A | 8/1988 | Kyle |
| 4,952,214 | A | 8/1990 | Comparetto |
| 5,122,146 | A * | 6/1992 | Chapman et al. ............ 606/102 |
| 5,607,431 | A * | 3/1997 | Dudasik et al. .............. 606/80 |
| 5,843,085 | A | 12/1998 | Graser |
| 6,190,390 | B1 * | 2/2001 | McAllister ................... 606/87 |
| 6,315,718 | B1 | 11/2001 | Sharratt |
| 6,551,325 | B2 | 4/2003 | Neubauer et al. |
| 6,676,706 | B1 * | 1/2004 | Mears et al. ................ 623/22.4 |
| 2001/0001120 | A1 * | 5/2001 | Masini ........................ 606/86 |
| 2002/0099447 | A1 | 7/2002 | Mears et al. |
| 2002/0116067 | A1 | 8/2002 | Mears et al. |
| 2002/0161446 | A1 | 10/2002 | Bryan et al. |
| 2003/0004513 | A1 | 1/2003 | Guzman et al. |
| 2003/0028196 | A1 * | 2/2003 | Bonutti ........................ 606/87 |
| 2003/0051362 | A1 | 3/2003 | Buckman et al. |
| 2003/0158559 | A1 | 8/2003 | Diaz |
| 2003/0182815 | A1 | 10/2003 | Carlson, II |
| 2003/0187458 | A1 | 10/2003 | Carlson, II |

* cited by examiner

*Primary Examiner* — Thomas C Barrett
*Assistant Examiner* — Sameh Boles
(74) *Attorney, Agent, or Firm* — Kilpatrick Townsend & Stockton LLP

(57) ABSTRACT

Methods and devices for performing hip replacement surgery are described. According to one embodiment, a method comprising providing an incision locator, the incision locator comprising at least one location indicator and at least one incision indicator, the location indicator configured to align with a central axis of the femur, and the incision indicator configured to guide a proper placement of a surgical incision when the location indicator is aligned, aligning the location indicator with at least one anatomical feature of the patient, making an incision in the proper location as guided by the incision indicator, and completing the surgical procedure is described.

8 Claims, 5 Drawing Sheets

HIP REPLACEMENT INCISION LOCATOR

RELATED APPLICATION

This is a continuation in part of U.S. application Ser. No. 10/775,561 filed Feb. 10, 2004 now U.S. Pat. No. 7,160,307 by David Hardwood et al. entitled "Hip Replacement Incision Locator."

FIELD OF THE INVENTION

The invention relates generally to devices for ensuring proper location for an incision for a surgical approach to a hip. In particular one embodiment discloses a method for determining a proper incision for hip replacement surgery.

BACKGROUND OF THE INVENTION

When beginning a surgical approach to the hip, such as during a hip replacement surgery for example, it is important for the surgeon to make the initial incision at the correct location. Incorrect placement or alignment of incisions can result in lengthening the incision, a greater loss of blood, and lengthened recovery times. To reduce the occurrence of incorrect incision placement, surgeons use diverse methods in their attempts to ascertain the internal placement of bones and joints, and thus the correct location for incision.

Some surgeons palpate the hip of a patient in order to find landmarks, which correspond with internal structures. Others use rulers, protractors, or other methods of measurement in an attempt to get as close as possible to the correct location. Still others may only extrapolate from past experiences and patients in their determination of the correct incision location.

These methods, however, can present obvious difficulties and disadvantages. Educated guesses, even made by surgeons with a long line of past experience, can result in incorrect placement. Devices and methods are therefore needed for ensuring proper placement of the initial incision in a total hip replacement surgery that are both accurate and reproducible.

SUMMARY OF THE INVENTION

Various embodiments of the present invention provide locators for proper placement of the initial incision when performing a total hip replacement surgery. According to one embodiment of the present invention, the incision locator is "V" shaped, having a first wing and a second wing that extend from a common point. According to another embodiment, the incision locator can comprise a guitar shaped device adapted to conform to the curvature of a patient's hip. According to other embodiments, the incision locator is any geometric shape in which placement of one portion along or in a known relationship to the femoral axis, or other suitable anatomical landmark, determines the proper incision location.

According to one aspect of the present invention, the incision locator is a one-piece design. In other embodiments, the incision locator can be formed from separate components. According to other embodiments, a first wing is adapted to be oriented generally along the femoral axis of a patient during hip replacement surgery. The position of the second wing is then used to generally identify the proper location and placement of the incision.

In other embodiments, the proper location of the first wing of the incision locator is determined through palpation of the patient's greater trochanter. In some embodiments, measurements are taken along the femoral axis to determine proper location. In still other embodiments, proper placement of the first wing is accomplished through the use of fluoroscopy.

In certain embodiments of the present invention, the angle formed by the first and second wings of the incision locator is approximately 30 degrees. In other embodiments, the angle is adjustable to account for differences in patient body shape or may be fixed at any suitable angle such as an angle ranging from substantially 20 degrees to 30 degrees or any other suitable angle producing a desired incision location.

In certain embodiments, lines or markings are drawn on the patient's skin indicating the femoral axis and the tip of the greater trochanter. In other embodiments, pins are used to mark the desired locations. The incisions may be made using devices according to various embodiments of the invention as a cutting guide or for marking where an incision should be made.

In certain embodiments of the present invention, the incision locater is used in conjunction with fluoroscopy, so that a surgeon or surgical assistant can locate the femoral axis and greater trochanter with precision. This embodiment of the present invention is especially useful where patient figure or other factors make palpation difficult, or when a more accurate internal alignment is needed.

Another embodiment of the present invention includes methods for performing hip replacement surgery through the use of the devices such as those described herein. In certain embodiments, a surgeon palpates a patient's hip to locate the greater trochanter and central axis of the femur. The surgeon can then align the device with the femoral axis or align the device to be parallel with the femoral axis. A wing portion of the device starts anterior and inferior to the greater trochanter and extends to a position posterior and superior to the greater trochanter. A surgeon can then use the device to locate a proper placement of an incision based at least in part on the position of the wing of the device, make an incision using an incision guide in the wing, and complete the surgical procedure. In other embodiments, a device indicating the proper placement for an incision for a lateral approach to the hip may be used. According to one embodiment, a non-flat device can be used to indicated a proper placement of a lateral approach to a left or right hip. According to one embodiment, the non-flat device can be substantially guitar-shaped.

DETAILED DESCRIPTION

Figure 1:
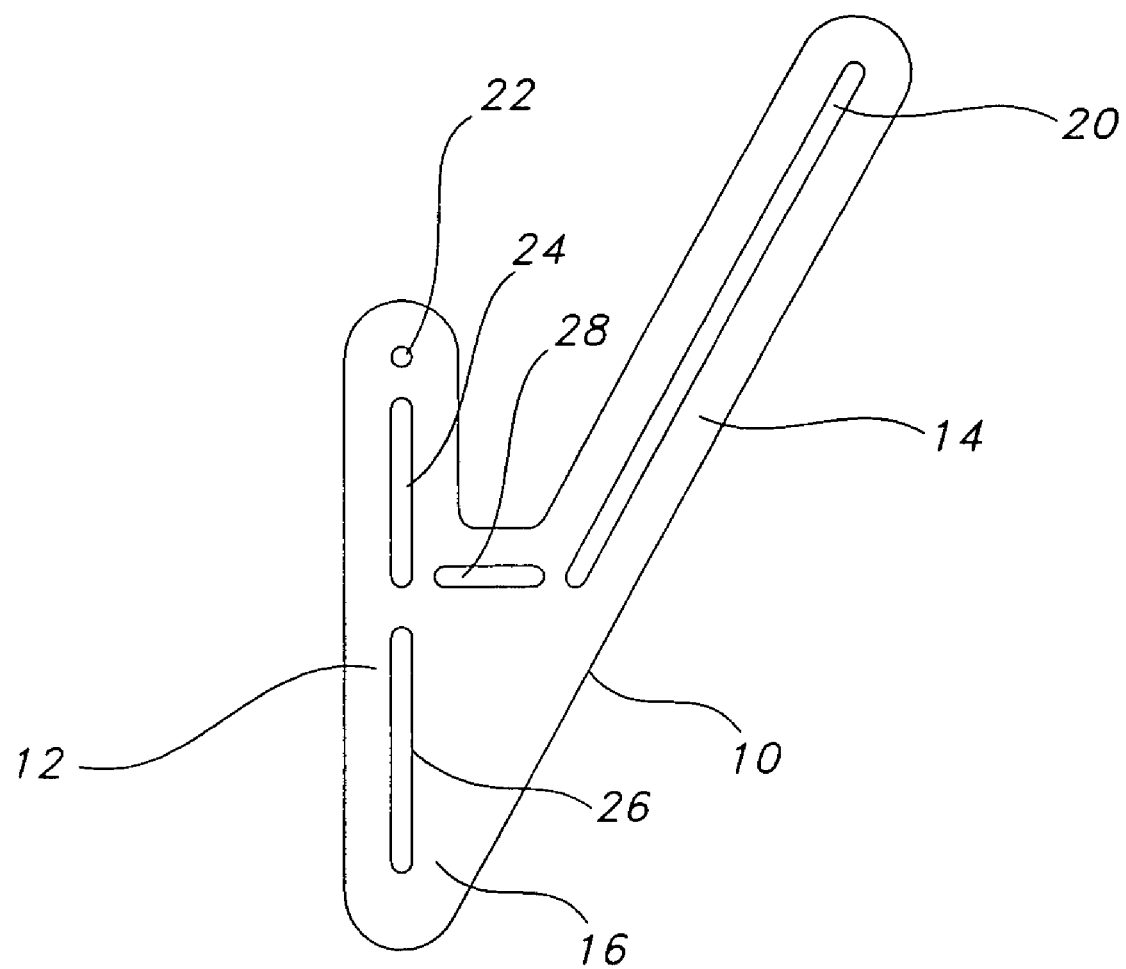
FIG. 1 illustrates a device according to one embodiment of the present invention.

Methods and devices according to certain embodiments of the present invention assist a surgeon to determine a proper initial incision when performing a surgical approach to the hip such as for a total hip replacement surgery. FIG. 1 shows a device according to one embodiment of the present invention comprising an incision locator 10. According to certain aspects of some embodiments of the present invention, the incision locator 10 comprises a first wing 12, a second wing 14, and a connecting portion 16. Alternatively, the first and second wing may comprise portions of an integral geometric shape such as a triangle, quadrilateral, or other suitable shape. According to aspects of certain embodiments, the second wing forms an angle with the first wing. According to certain embodiments, the angle can be substantially a thirty-degree angle. According to other embodiments, the angle can be substantially a twenty-degree angle, or any suitable angle ranging from substantially 20 degrees to substantially 30 degrees as determined by clinical experience for producing a desired incision location. Generally, the angle is a matter of choice and may include any suitable range of angles that may vary depending on a surgeon's preference. For example, a surgeon may discover a suitable angle for locating an initial incision for a surgical approach to the hip and devices according to the present invention can comprise that angle.

According to aspects of other embodiments, the first wing and second wing may be attached at a pivoting point allowing a variety of angles to be selected in order to accommodate differences in patient physique.

According to aspects of the embodiment depicted in FIG. 1, the first wing 12 comprises a first incision locator 22, a second incision locator 24, and a third incision locator 26. In use, the incision locators can be used to assist a surgeon in orienting the incision locator 10 with anatomical features. According to aspects of other embodiments, fewer incision locators may be used or more incision locators may be used.

According to the embodiment depicted in FIG. 1, the second wing 14 comprises an incision locator 20. According to certain aspects of the embodiment depicted in FIG. 1, the incision locator 20 of the second wing 14 is ten centimeters in length. In use, the incision locator 20 can be used by a surgeon to determine a proper incision for a surgical approach to the hip such as during a hip replacement surgery.

Figure 2:
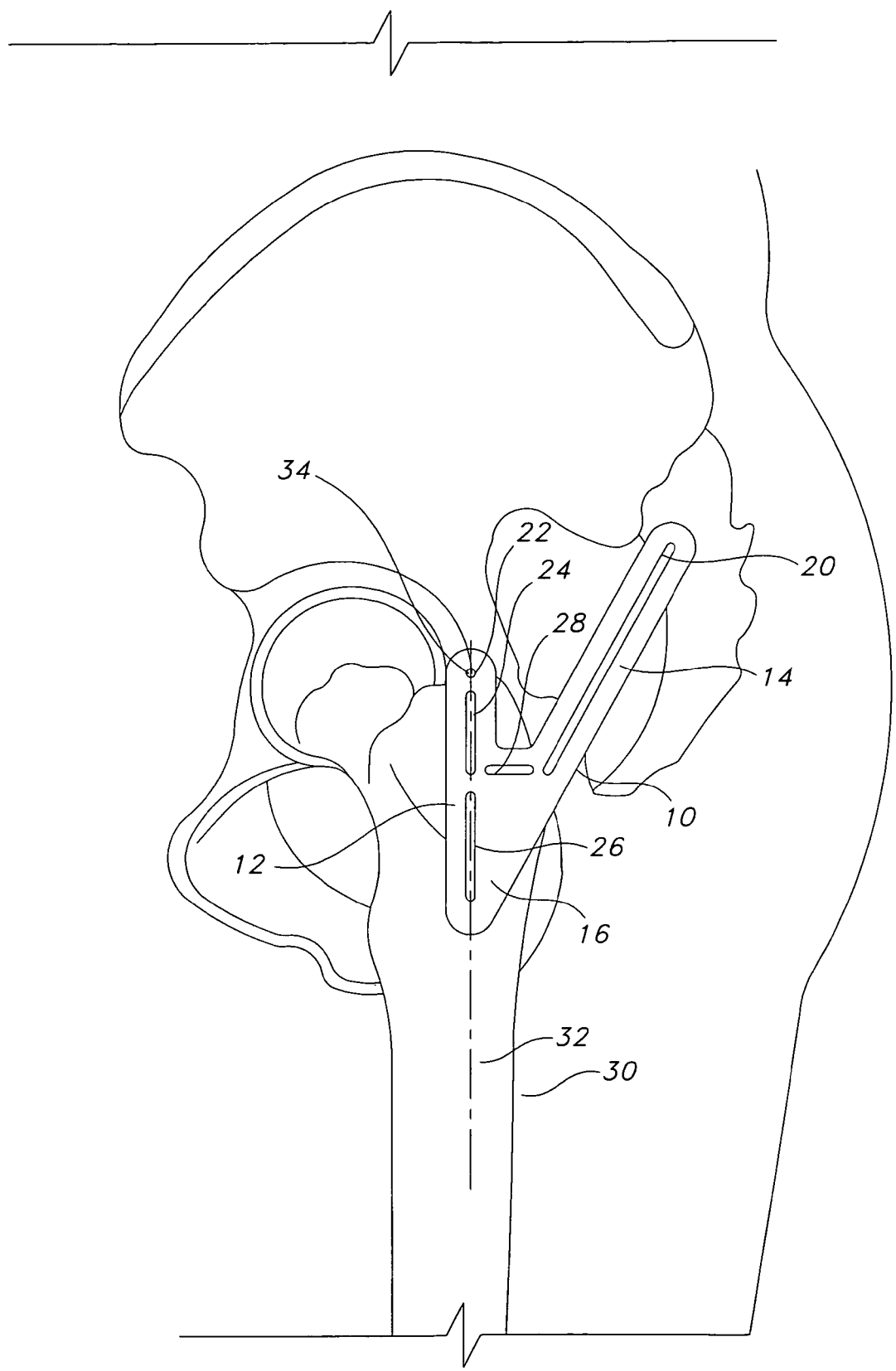
FIG. 2 illustrates the device of FIG. 1 positioned in proper alignment to determine an incision point for a hip replacement surgery.

According to the certain aspects of the embodiment depicted in FIG. 2, the incision locator 20 can determine a proper incision for a posterior approach in a hip replacement surgery. Other suitable approaches may be determined according to other aspects of embodiments of the present invention. For example, methods and devices for a lateral approach are possible in accordance with embodiments of the present invention and are discussed in greater detail in connection with FIGS. 4 and 5. According to aspects of other embodiments, the incision locator 20 of the second wing 14 can be any other suitable length as determined by clinical experience, clinical trials, or other appropriate method.

According to the embodiment depicted in FIG. 1, the connecting portion 16 is substantially triangular in shape, or, alternatively, another suitable shape. According to other embodiments, the connecting portion could comprise a portion of an integral geometric shape which can comprise the first wing 12 and the second wing 14. The connecting portion 16, according to the embodiment depicted in FIG. 1, further comprises an incision guide 28. In the embodiment depicted in FIG. 1, the incision guide 28 is substantially perpendicular to the first, second, and third incision locators 22, 24, and 26 of the first wing 12.

FIG. 2 illustrates a lateral view of a patient's leg with the incision locator 10 in place. The patient's leg illustrated in FIG. 2 comprises a femur 30, a femoral axis 32, and a greater trochanter of the center femur 34. For illustration purposes, methods in accordance with the present invention will be explained in connection with FIG. 2. To determine a proper placement of an incision for a hip replacement surgery, a surgeon, or other suitable person, can palpate a patient's leg and locate the tip of the greater trochanter 34. According to certain embodiments, the surgeon can mark the location of the tip of the greater trochanter 34 with a marking device such as a pin, skin marking, or other suitable method.

Once the position of the tip of the greater trochanter 34 is determined, the surgeon can determine the position of the center of the femur and make a marking, such as a line on the surface of the patient's leg, indicating the femoral axis 32. According to other embodiments of the present invention, the surgeon may use fluoroscopy, magnetic resonance imaging, anatomical measurements, or other suitable imaging or measuring techniques in addition to, or in place of, palpation to determine proper placement of the incision locator 10, and/or the position of the tip of the greater trochanter 34, and/or the position of the femoral axis 32.

Once the surgeon determines and indicates the position of the tip of the greater trochanter 34 and the femoral axis 32 by palpation, measuring, imaging, or other suitable method, the incision locator is placed on the patient's leg in the area of the greater trochanter 34. According to the embodiment depicted in FIG. 2, the first wing 12 is placed in the area of the femoral axis 32 and the second wing 14 is pointed posteriorly. The surgeon then aligns one or more of the incision guides with the tip of the greater trochanter 34. According to aspects of the embodiment depicted in FIG. 2 for illustration purposes, the first incision guide 22 of the first wing 12 is aligned with the tip of the greater trochanter 34 using the pin or other suitable marking used to indicated the location of the tip of the greater trochanter 34.

After aligning the tip of the greater trochanter with the first incision guide 22, according to aspects of the embodiment depicted in FIG. 2, the surgeon then aligns the femoral axis 32 with the second and third incision guides 24 and 26 of the first wing 12. With the incision locator 10 on the patient's leg, the first incision guide aligned with the tip of the greater trochanter 34, and the second and third incision guides aligned with the femoral axis 32, the incision guide 20 of the second wing 14 of the incision locator 10 indicates a proper placement of an incision. According to the embodiment shown in FIG. 2, the incision guide 20 indicates a proper position for a ten-centimeter incision for a posterior approach for a hip replacement procedure.

Figure 3:
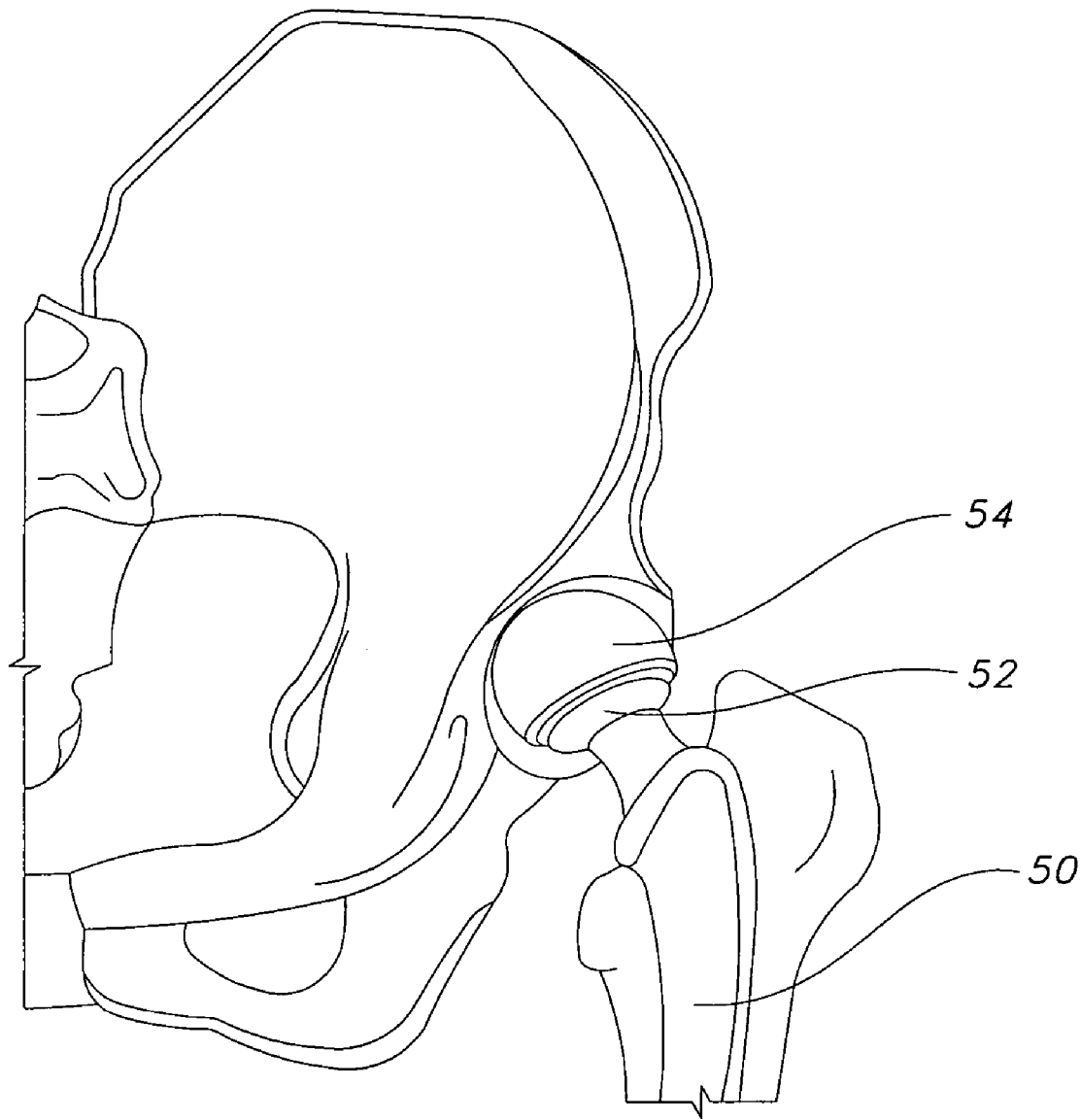
FIG. 3 illustrates aspects of hip replacement surgery conducted with devices and methods according to certain embodiments of the invention.

With the incision locator 10 in place, the surgeon can either mark the placement of the incision through the incision guide 20, remove the incision locator 10, and proceed to make an incision along the mark indicating the placement of the incision, or alternatively, the surgeon can make the incision with the incision locator 10 in place, using the incision guide 20 to guide the cutting instrument. Once the incision is performed, the surgeon can proceed to perform a surgical procedure on the hip, such as a hip replacement procedure, according to standard surgical procedure. For example, the surgeon can proceed to perform a hip replacement procedure including placing and installing components such as a femoral hip replacement component 50, a femoral stem 52, and an acetabular cup 54 as illustrated in FIG. 3.

Figure 4:
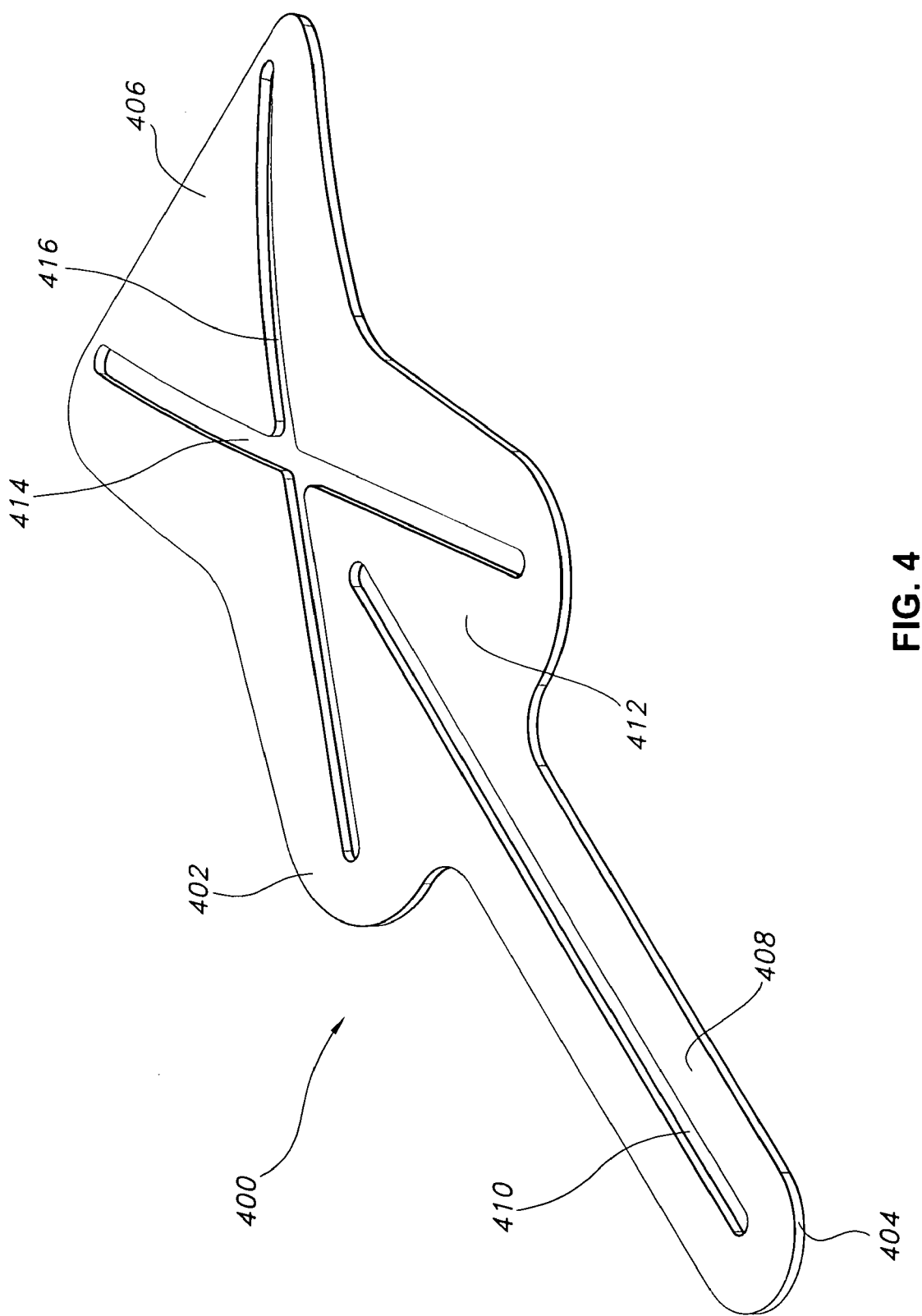
FIG. 4 illustrates another device according to one embodiment of the present invention.

FIG. 4 illustrates certain aspects of one embodiment of the present invention allowing for a lateral orthopedic approach to the hip. The Incision locator 400 illustrated in FIG. 4 comprises a surface 402 comprising a distal end 404 and a proximal end 406. According to the embodiment depicted in FIG. 4, the distal end 402 comprises an elongated neck 408. The elongated neck comprises a locator opening 410 extending lengthwise along the neck. The elongated neck 408 extends proximally to join with a wider body portion 412. The body portion 412 continues proximally to terminate at the proximal end 406. The body portion 412 comprises incision indicators 414 and 416. According to the embodiment depicted in FIG. 4, the incision indicators 414 and 416 cross to form an X-shaped pattern. According to other embodiments, the incision locator 400 may comprises only a single incision locator.

The incision indicators 414 and 416 depicted in FIG. 4 comprise openings in the surface 402. According to other embodiments, the incision indicators 414 and 416 can comprises a transparent portion of the surface 402, a mesh portion of the surface 402, or other suitable structure for indicating the proper placement of an incision at the desired anatomical point. The body portion 412 can be configured to conform to a lateral surface of a patient's leg near the greater trochanter. The body portion 412 depicted in FIG. 4 narrows towards a center of the body in between the proximal end 406 and where the neck 408 joins the body 412. The narrow neck 408 in combination with the wider body 412, and the narrowing of the body 412 towards the center of the body gives the incision locator 400 a guitar-shaped appearance. Persons skilled in the art will appreciated that other suitable shapes can be used in keeping with the present invention and the guitar-shaped embodiment is but one exemplary embodiment that may be used. The proximal end 406 of the incision locator 400 can be curved posteriorly to better conform to the surface of a patient's leg in the area of the greater trochanter.

Figure 5:
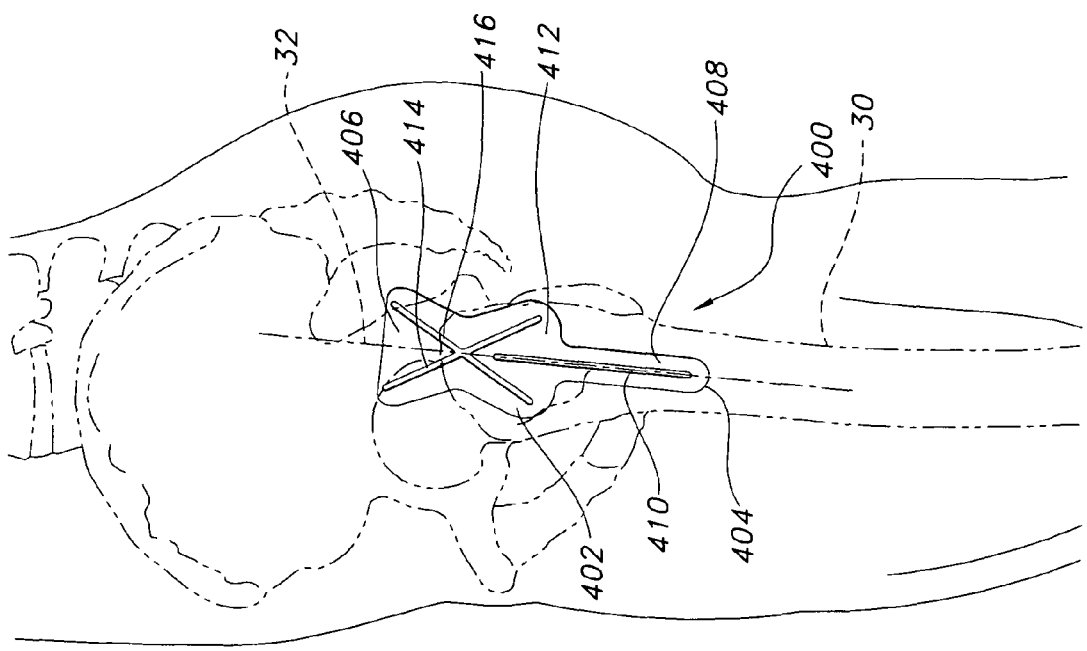
FIG. 5 illustrates the device of FIG. 4 positioned in proper alignment to determine an incision point for a hip replacement surgery

In use the incision locator 400 is placed on the lateral surface of a patient's leg with the proximal end 406 in the area of the greater trochanter as illustrated in FIG. 5. The locator opening 410 of the neck 408 can then be aligned with a central axis 32 of the femur 30. According to the embodiment depicted in FIG. 4, the incision locator 400 is bilaterally symmetric to facilitate use on either a left of right hip. According to other embodiment, the incision locator 400 may not be bilaterally symmetric and can be designed exclusively for a left or right hip. Once placed on the skin in the area of the greater trochanter with the central axis 32 of the femur 30 aligned with the location opening 410, a surgeon can use the incision indicators 414 and 416 to determine the proper placement for an incision.

With the incision locator 400 in place, the surgeon can either mark the placement of the incision through the incision indicators 412 and 414, remove the incision locator 400, and proceed to make an incision along the mark indicating the placement of the incision, or alternatively, the surgeon can make the incision with the incision locator 400 in place, using the incision indicators 412 and 414 to guide the cutting instrument. Once the incision is performed, the surgeon can proceed to perform a surgical procedure on the hip, such as a hip replacement procedure, according to standard surgical procedure. For example, the surgeon can proceed to perform a hip replacement procedure including placing and installing components such as a femoral hip replacement component 50, a femoral stem 52, and an acetabular cup 54 as illustrated in FIG. 3.

The foregoing has been provided for purposes of disclosure of preferred embodiments of the invention. Changes, additions, omissions may be made to the devices and processes disclosed in this document without departing from the scope or spirit of the invention.

What is claimed is:

1. A method for locating a site on a patient's hip suitable for establishing a proper skin incision for a surgical approach to a hip for performing a hip arthroplasty, the method comprising:

providing an incision locator, the incision locator comprising at least one location indicator and at least one incision indicator at an oblique angle with respect to a line extending along said location indicator, the location indicator configured to conform to the patient's skin along an external surface of the patient's hip and to align with an anatomical feature, and the incision indicator configured to guide a proper placement of an opening surgical skin incision for a surgical approach to the hip for the hip arthroplasty when the location indicator is aligned, wherein the location indicator is configured to align with said anatomical feature prior to making any incision and the incision indicator is configured to guide a proper placement of an opening surgical skin incision prior to making any incision, such that the location indicator and incision indicator are both capable of being used before any other incision is made;

identifying an external landmark indicating the location of the anatomical feature;

aligning the location indicator with the anatomical feature;

making an opening skin incision at an oblique angle to the line extending along the location indicator and in the proper location for the surgical approach for the hip arthroplasty as guided by the incision indicator; and completing the surgical procedure.

2. The method of claim 1, wherein the anatomical feature is one of a central axis of the femur and a line parallel to the central axis of the femur.

3. The method of claim 2, wherein the incision locator comprises:

a superior portion and an inferior portion, the superior portion comprising the at least one incision indicator configured to indicate a proper incision for a lateral approach to the hip and configured to conform to a patient's leg in the area of the greater trochanter, and the inferior portion comprising the at least one location indicator, and configured to align with the central axis of the femur.

4. The method of claim 3, wherein the location indicator comprises one or more opening in the template.

5. The method of claim 3, wherein the incision locator comprises an opening in the template configured to guide a cutting instrument.

6. The method of claim 3, wherein the incision indicator is configured to indicate a 10 centimeter incision.

7. The method of claim 3, wherein the inferior portion forms a narrow portion extending from the superior portion, whereby the template is substantially guitar-shaped.

8. The method of claim 3, wherein the location indicator comprises one or more transparent portion in the template.

* * * * *